United States Patent
Cho et al.

(10) Patent No.: US 11,925,726 B2
(45) Date of Patent: Mar. 12, 2024

(54) PERFUSABLE-TYPE DUAL PROXIMAL TUBULE CELL CONSTRUCT AND PRODUCING METHOD THEREOF FOR APPLYING IN VITRO ARTIFICIAL RENAL TISSUE MODEL AND RENAL CELL THERAPY

(71) Applicants: POSTECH Research and Business Development Foundation, Pohang-si (KR); THE CATHOLIC UNIVERSITY OF KOREA INDUSTRY-ACADEMIC COOPERATION FOUNDATION, Seoul (KR)

(72) Inventors: Dong-Woo Cho, Seoul (KR); Wonil Han, Pohang-si (KR); Narendra K. Singh, Pohang-si (KR); Yong Kyun Kim, Seongnam-si (KR); Sun Ah Nam, Gimpo-si (KR)

(73) Assignees: POSTECH RESEARCH AND BUSINESS DEVELOPMENT FOUNDATION, Pohang-si (KR); THE CATHOLIC UNIVERSITY OF KOREA INDUSTRY—ACADEMIC COOPERATION FOUNDATION, Seoul (KR)

( * ) Notice: Subject to any disclaimer, the term of this patent is extended or adjusted under 35 U.S.C. 154(b) by 559 days.

(21) Appl. No.: 17/126,449

(22) Filed: Dec. 18, 2020

(65) Prior Publication Data
US 2022/0072203 A1    Mar. 10, 2022

(30) Foreign Application Priority Data
Sep. 7, 2020 (KR) .......................... 10-2020-0113999

(51) Int. Cl.
| | | |
|---|---|---|
| A61L 27/38 | (2006.01) | |
| A61F 2/02 | (2006.01) | |
| A61L 27/36 | (2006.01) | |
| C12N 5/00 | (2006.01) | |
| C12N 5/071 | (2010.01) | |

(52) U.S. Cl.
CPC .......... *A61L 27/3839* (2013.01); *A61F 2/022* (2013.01); *A61L 27/3641* (2013.01); *A61L 27/3683* (2013.01); *A61L 27/3886* (2013.01); *C12N 5/0685* (2013.01); *C12N 5/0686* (2013.01); *C12N 5/069* (2013.01); *C12N 5/0697* (2013.01)

(58) Field of Classification Search
None
See application file for complete search history.

(56) References Cited

U.S. PATENT DOCUMENTS

| | | | |
|---|---|---|---|
| 2019/0284517 A1 | 9/2019 | Jeong et al. | |
| 2020/0063107 A1* | 2/2020 | Kong | A61F 2/06 |
| 2020/0164109 A1* | 5/2020 | Kroll | A61L 27/28 |

FOREIGN PATENT DOCUMENTS

| | | |
|---|---|---|
| KR | 10-2017-0064547 | 6/2017 |
| KR | 10-2018-0124560 | 11/2018 |
| KR | 102026326 | 9/2019 |

OTHER PUBLICATIONS

Lin et al., PNAS, 2019 (Mar. 19), vol. 116, No. 12, pp. 5399-5404. (Year: 2019).*
Narendra K. Singh et al., "Three-dimensional cell-printing of advanced renal tubular tissue analogue", Biomaterials, vol. 232, Feb. 2020, 119734. https://doi.org/10.1016/j.biomaterials.2019.119734.
KIPO, Office Action of KR 10-2020-0113999 dated Jan. 12, 2022.

* cited by examiner

*Primary Examiner* — Allison M Fox
(74) *Attorney, Agent, or Firm* — LEX IP MEISTER, PLLC

(57) ABSTRACT

The present disclosure is related to a perfusable-type bio-dual proximal tubule cell construct and a producing method thereof capable of applying an in vitro artificial organ model configured to include a first bioink comprising a decellularized substance derived from a mammalian kidney tissue and human umbilical vascular endothelial cells (HUVECs) and a second bioink comprising the decellularized substance and renal proximal tubular epithelial cells (RPTECs), wherein the first bioink and the second bioink are coaxial and printed in tubular constructs having different inner diameters.
According to the present disclosure, it is possible to use the renal proximal tubule-on-a-chip as a bioreactor capable of observing a biological drug reaction similar to a real drug by perfusing various drugs to the renal proximal tubule-on-a-chip.

20 Claims, 27 Drawing Sheets

US 11,925,726 B2

PERFUSABLE-TYPE DUAL PROXIMAL TUBULE CELL CONSTRUCT AND PRODUCING METHOD THEREOF FOR APPLYING IN VITRO ARTIFICIAL RENAL TISSUE MODEL AND RENAL CELL THERAPY

CROSS-REFERENCE TO RELATED APPLICATIONS

Priority to Korean patent application number 10-2020-0113999 filed on Sep. 07, 2020 the entire disclosure of which is incorporated by reference herein, is claimed.

BACKGROUND OF THE DISCLOSURE

Field of the disclosure

The present disclosure relates to a perfusable-type proximal tubule cell construct and a producing method thereof capable of applying an in vitro artificial organ model, and more particularly, to a bio-dual renal tubular construct capable of perfusion and implantation.

Related Art

Recently, in the field of tissue engineering/regenerative medicine, research on the development of a bioartificial kidney as an in vitro kidney model for application to drug testing or as a cell-based therapeutic agent for application to regenerative medicine has been actively conducted. However, most kidney constructs which have been reported to date have a form of randomly encapsulating cells existing at partitioned positions in an actual kidney in a hydrogel-type biomaterial, and thus, it is impossible to implement the characteristics of the actual kidney to which a tubular construct-based microfluidic environment is applied. In addition, in the case of perfusable renal constructs which have been recently reported, there is an advantage of better recapitulating the microstructure and functions of the kidney. However, in this case, since all of the perfusable renal constructs are in the form of organ-on-a-chip and are integrated with synthetic polymers, there is a problem that it is impossible to separate only the kidney constructs and extend to apply the separated kidney constructs for regenerative medicine.

Meanwhile, such a microfluidic chip is disclosed in Korean Patent Registration No. 2026326.

SUMMARY OF THE DISCLOSURE

An object of the present disclosure is to provide a perfusable-type proximal tubule cell construct and a producing method thereof capable of applying an in vitro renal tissue model to solve the problems of conventional cell-based renal tissue constructs.

In an aspect, a perfusable-type bio-dual proximal tubule cell construct capable of applying an in vitro artificial organ model is provided. The perfusable-type bio-dual proximal tubule cell construct capable of applying the in vitro artificial organ model may be configured to include a first bioink produced by containing a decellularized substance derived from a mammalian kidney tissue and human umbilical vascular endothelial cells (HUVECs) and a second bioink containing the decellularized substance and renal proximal tubular epithelial cells (RPTECs), wherein the first bioink and the second bioink may be coaxial and printed in tubular constructs having different inner diameters.

Meanwhile, the first bioink may be printed to configure a first tubular construct, the second bioink may be printed to configure a second tubular construct, and at least a part of an outer surface of the first tubular construct may be configured to be in contact with an inner surface of the second tubular construct.

The first bioink and the second bioink may be configured to include alginate so as to reduce a shape change after printing.

The first bioink and the second bioink may be configured to contain the decellularized substance in a concentration of 20 mg/ml to 40 mg/ml and the alginate in a concentration of 5 mg/ml to 15 mg/ml.

The decellularized substance may be produced in the form of a hydrogel by lyophilizing the kidney tissue, treating the lyophilized kidney tissue with 0.3 M to 0.7 M of an acetic acid solution, and neutralizing the treated kidney tissue with 5 M to 15 M NaOH.

The first tubular construct and the second tubular construct may be simultaneously printed by a 3D printer provided with a coaxial double nozzle.

The perfusable-type bio-dual proximal tubule cell construct may further include a support configured to support the first tubular construct from the inner side of the first tubular construct and configured to be removed when the tubule cell construct is cultured.

The support may be printed on the inner side of the first tubular construct while being coaxial with the first tubular construct and the second tubular construct.

The support may contain Pluronic F127 (polyethylene oxide-b-polypropylene oxide-b-polyethylene oxide).

In another aspect, an renal proximal tubule-on-a-chip capable of applying an in vitro artificial organ model is provided. The renal proximal tubule-on-a-chip capable of applying an in vitro artificial organ model may include a vascular tubule construct which is printed with a first bioink produced by containing a decellularized substance derived from a mammalian kidney tissue and human umbilical vascular endothelial cells (HUVECs) and configured in a tubular shape; and a proximal tubule construct which is printed with a second bioink containing the decellularized substance and renal proximal tubular epithelial cells (RPTECs) and configured in a tubular shape, wherein the vascular tubule construct and the proximal tubular construct may be at least partially printed in parallel with each other and configured so that the outer surfaces thereof are in contact with each other.

The renal proximal tubule-on-a-chip may further include a case provided with a space in which the vascular tubule construct and the proximal tubule construct are printed.

The case may include an artificial proximal tubule part configured to dispose a part of the vascular tubule construct and a part of the proximal tubule construct which are in contact with each other; and multiple fixing parts configured to fix both ends of the vascular tubule construct and both ends of the proximal tubule construct, respectively.

The vascular tubule construct may be printed by including a support that is coaxial with the first bioink and printed together on the inner side of the tubular part when the first bioink is printed, and configured by removing the support after printing.

The proximal tubule construct may be printed by including a support that is coaxial with the second bioink and printed together on the inner side of the tubular part when the second bioink is printed, and formed by removing the support after printing.

In yet another aspect, a producing method of a proximal tubule cell construct is provided. The producing method of a proximal tubule cell construct may include the steps of:

producing a decellularized substance derived from a mammalian kidney tissue; extracting and preparing human umbilical vascular endothelial cells (HUVECs) and renal proximal tubular epithelial cells (RPTECs) from a living kidney tissue; producing a first bioink containing the decellularized material and the HUVECs; producing a second bioink containing the decellularized material and the RPTECs; printing a vascular tubule construct using the first bioink; and printing a proximal tubule construct using the second bioink, wherein the printing of the vascular tubule construct and the printing of the proximal tubule construct may be performed while the vascular tubule construct and the proximal tubule construct are at least partially in contact with each other.

The printing of the vascular tubule construct and the printing of the proximal tubule construct may be performed using a coaxial triple nozzle, and a support on a central side, the vascular tubule construct on the outer side of the support, and the proximal tubule construct on the outer side of the vascular tubule construct may be simultaneously printed coaxially.

The printing of the vascular tubule construct may be performed using a coaxial double nozzle, and performed by printing a support configured to support the vascular tubule construct from the inner side of the vascular tubule construct simultaneously with the vascular tubule construct.

The printing of the proximal tubule construct may be performed using a coaxial double nozzle, and performed by printing a support configured to support the proximal tubule construct from the inner side of the proximal tubule construct simultaneously with the proximal tubule construct.

The printing of the vascular tubule construct and the printing of the proximal tubule construct may be performed while the vascular tubule construct and the proximal tubule construct are at least partially parallel to each other and the outer surfaces thereof are in contact with each other.

The producing method of the proximal tubule cell construct may further include removing the support.

DESCRIPTION OF EXEMPLARY EMBODIMENTS

Figure 1A:
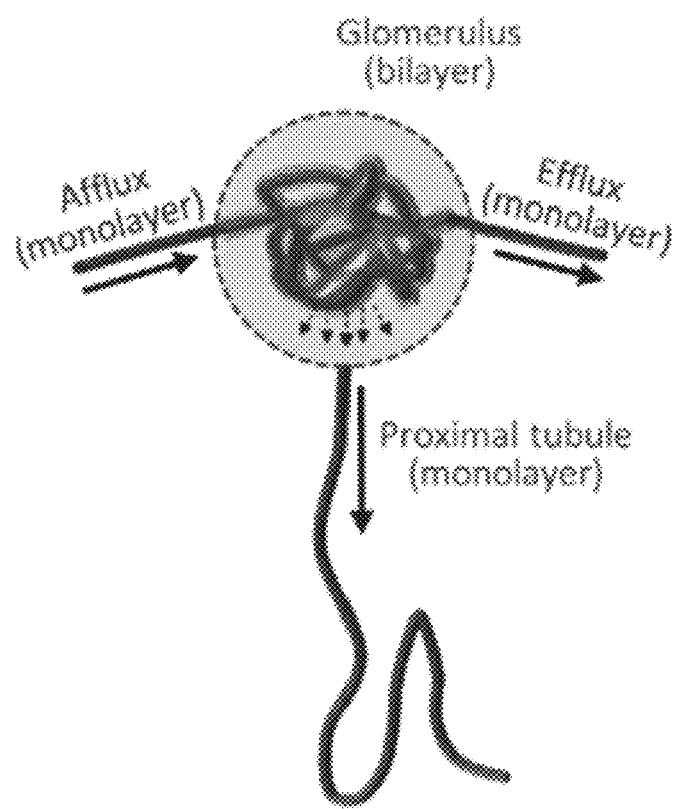
FIG. 1A and FIG. 1B are schematic diagrams of a glomerulus and a proximal tubule construct of the kidney and a diagram illustrating a 3D-printed construct thereof.

Hereinafter, a perfusable-type proximal tubule cell construct and a producing method thereof capable of applying an in vitro artificial organ model according to an embodiment of the present disclosure will be described in detail with reference to the accompanying drawings. In addition, in the description of the following embodiments, the name of each component may be referred to as another name in the art. However, if these components have functional similarities and identities, even if a modified embodiment is employed, the components may be considered as an equal configuration. In addition, symbols added to each component are described for convenience of description. However, the contents illustrated on the drawings in which these symbols are indicated do not limit each component to the range within the drawings. Likewise, even if an embodiment in which the configuration in the drawings is partially modified is employed, if there is functional similarity and identity, the configuration may be considered as an equal configuration. In addition, in the light of the level of those skilled in the art, if it is recognized as a component that should be included, a description thereof will be omitted.

Figure 1B:
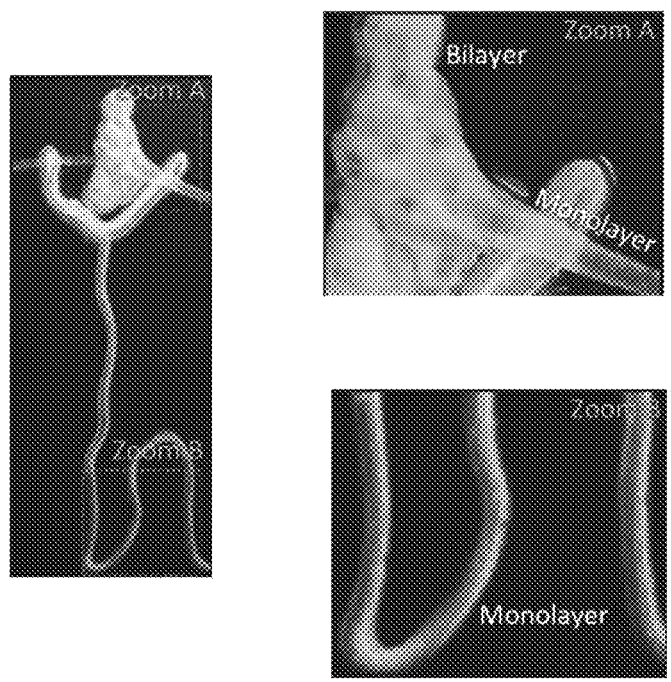

FIG. 1A and FIG. 1B are schematic diagrams of a glomerulus and a proximal tubule construct of the kidney and a diagram illustrating a 3D-printed construct thereof.

Referring to FIG. 1A, the human kidney has a glomerulus, which is a capillary bundle in a Bowman's capsule, and the glomerulus inhibits the transmission of substances of 8 nm or more, and transmits small substances of 4 nm or less, and the transmitted substances move toward a proximal tubule. In the proximal tubule, liquids and substances required for the human body are reabsorbed toward the blood vessels to maintain homeostasis in the body. It has been found that the glomerulus consists of a construct including a bilayered construct, and the proximal tubule consists of a construct including a single tubular construct.

Referring to FIG. 1B, the present disclosure may provide a method of producing a construct capable of reproducing a microstructure of the kidney, and a construct in which the microstructure of the kidney produced by the method is reproduced.

Hereinafter, a concept of a bioink used in the present disclosure will be described with reference to FIGS. 2 and 3.

Figure 2A:
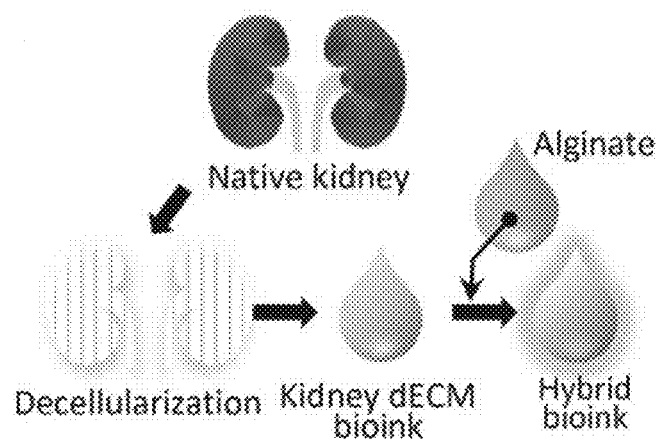
FIG. 2A and FIG. 2B are schematic diagrams illustrating a concept of producing a first bioink and a second bioink.
Figure 2B:
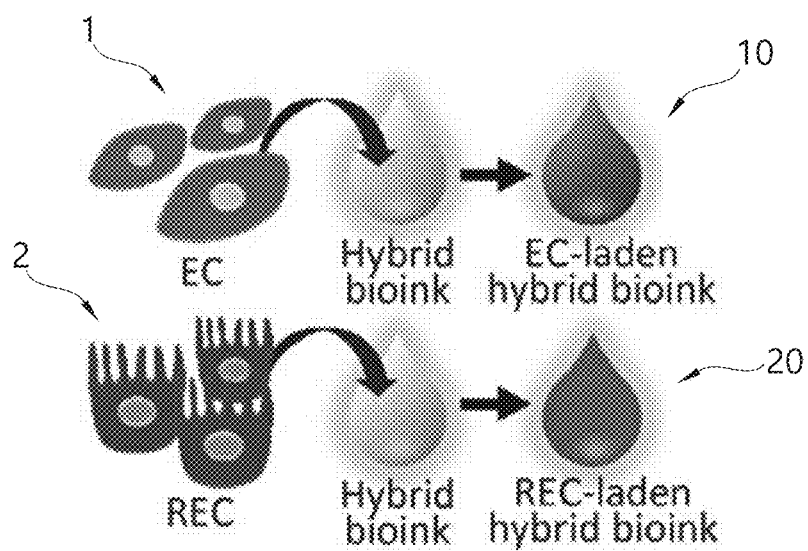

FIG. 2A and FIG. 2B are schematic diagrams showing a concept of producing a hybrid bioink.

Referring to FIG. 2A and FIG. 2B, a hydrogel used in the present disclosure may produce a decellularized substance from tissues collected from a mammalian kidney. Since the decellularized substance derived from the kidney tissue contains multiple tissue-specific ingredients to create an environment suitable for survival and proliferation when the cells collected from the kidney are cultured later. The decellularized substance derived from the kidney tissue is mixed with alginate so as to maintain adequate rigidity during 3D printing to produce a hybrid bioink. Meanwhile, matters related to the mixing of alginate will be described below with reference to FIG. 4A and FIG. 4B.

The decellularized substance was performed to maximize its suitability as a functional biomaterial, and a process of decellularizing the tissue extracted from the kidney of a pig was performed according to a method shown in the following table.

| Process | Hour |
|---|---|
| Slicing | — |
| Distilled water | 2 hours |
| 1% Triton X-100 in PBS | 12 hours |
| Distilled water | 2 to 4 hours |
| DNase (37° C.) | 7 hours |
| Distilled water | 2 to 4 hours |
| 0.1% peracetic acid in PBS | 1 hour |
| Distilled water | 2 hours |

The decellularized substance produced according to the process is a representative substance of cell ingredients, in which DNA exists in a small amount of less than 3%, and extracellular matrix ingredients such as glycosaminoglycan (GAG) and collagen are abundantly contained. In addition, in the decellularized substance, specific substances in the kidney tissue abundantly exist to create an optimal environment when the cells extracted from the kidney tissue are cultured.

The hybrid bioink may be produced by performing lyophilization and neutralization of the produced decellularized material.

The lyophilization corresponds to a step of lyophilizing the kidney tissue to form a powder. As an example, the neutralization may be performed by solubilizing the lyophilized decellularized material using 0.3 M to 0.7 M, preferably 0.5 M of an acetic acid solution and pepsin (protease) at 5 M to 15 M of NaOH, preferably 10 M of NaOH. The decellularized material subjected to the neutralization may produce a hydrogel-type kidney decellularized extracellular matrix (kdECM) bioink capable of finally encapsulating cells. In the present disclosure, the bioink produced from the decellularized substance may have a property which is fluid at 4° C. and gelled at 37° C. to maintain its shape.

Referring to FIG. 2B, after the hybrid bioink is produced, so as to reproduce and produce the proximal tubule construct, human umbilical vascular endothelial cells (HUVECs, EC) 1 are encapsulated in the hybrid bioink produced in FIG. 2A to produce first bioink 10 and renal proximal tubular epithelial cells (RPTECs, REC) 2 are encapsulated in the hybrid bioink to produce second bioink 20, respectively. The first bioink 10 and the second bioink 20 are three-dimensionally printed, and may be printed coaxially or as a single tubular construct.

Figure 3A:
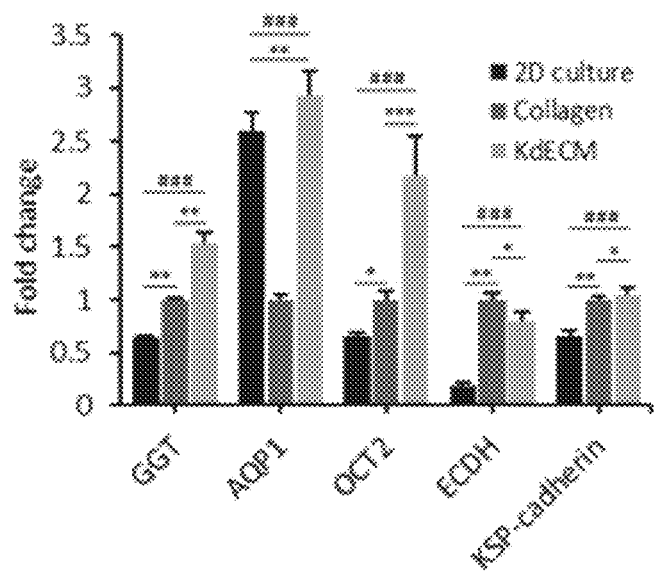
FIG. 3A, FIG. 3B and FIG. 3C are graphs showing an effect of treating a proximal
tubule using the first bioink.
Figure 3B:
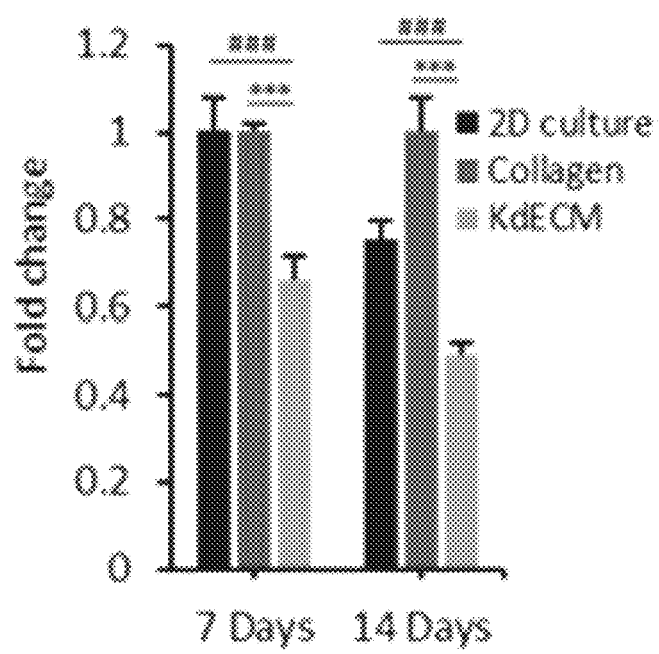
Figure 3C:
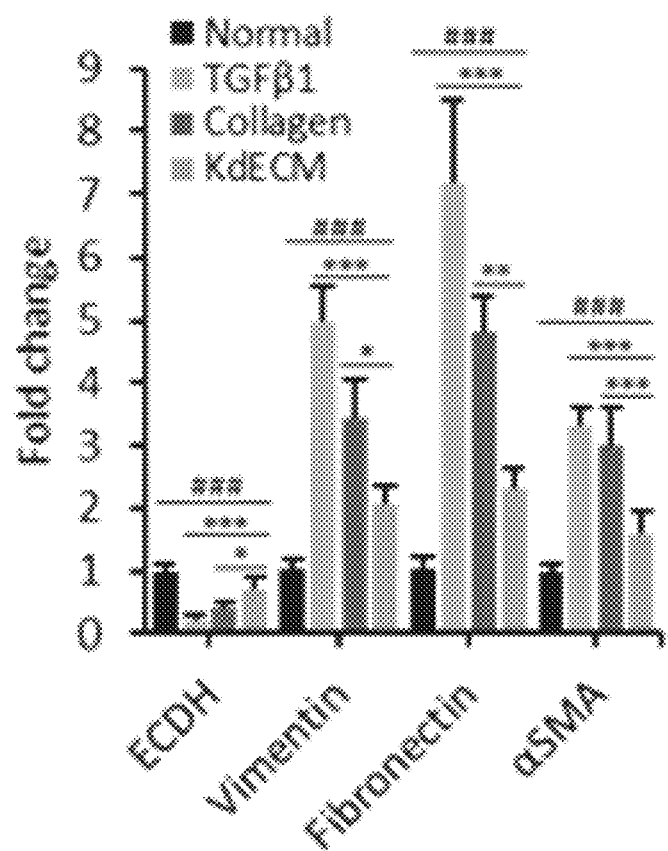

FIG. 3A, FIG. 3B and FIG. 3C are graphs showing an effect of treating the proximal tubule using the first bioink 10.

Referring to FIG. 3A, FIG. 3B and FIG. 3C, the first bioink 10 was produced by encapsulating the HUVECs 1 in the hybrid bioink, and its functionality was compared with that of an experimental group using a medical collagen bioink. Referring to FIG. 3A, it was confirmed that in an experimental group using the first bioink 10, the expression of markers GGT, AQP1, OCT2, ECDH, and KSP-cadherin for the proximal tubule function was increased. In addition, referring to FIG. 3B, it was confirmed that the expression of a kidney injury marker KIM1 was lowered. In addition, referring to FIG. 3C, when kdECM bioink was treated on proximal tubule cells in which fibrotic injury was induced using TGFb, it was confirmed that the symptoms were recovered (the ECDH expression increased and the expression of vimentin, fibronectin, and maSMA decreased), and thus, it may be confirmed that the kdECM bioink has a therapeutic function for injury kidney cells.

Figure 4A:
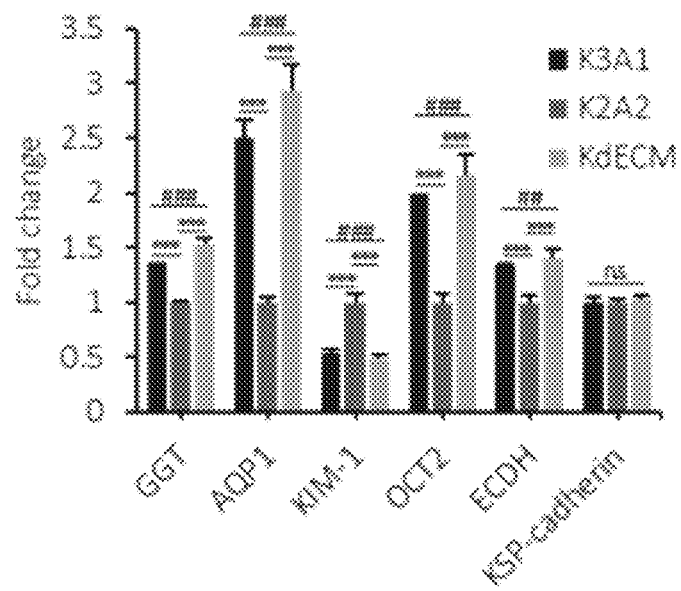
FIG. 4A and FIG. 4B are diagrams illustrating results of confirming a mixing ratio and cytotoxicity of a hybrid bioink.
Figure 4B:
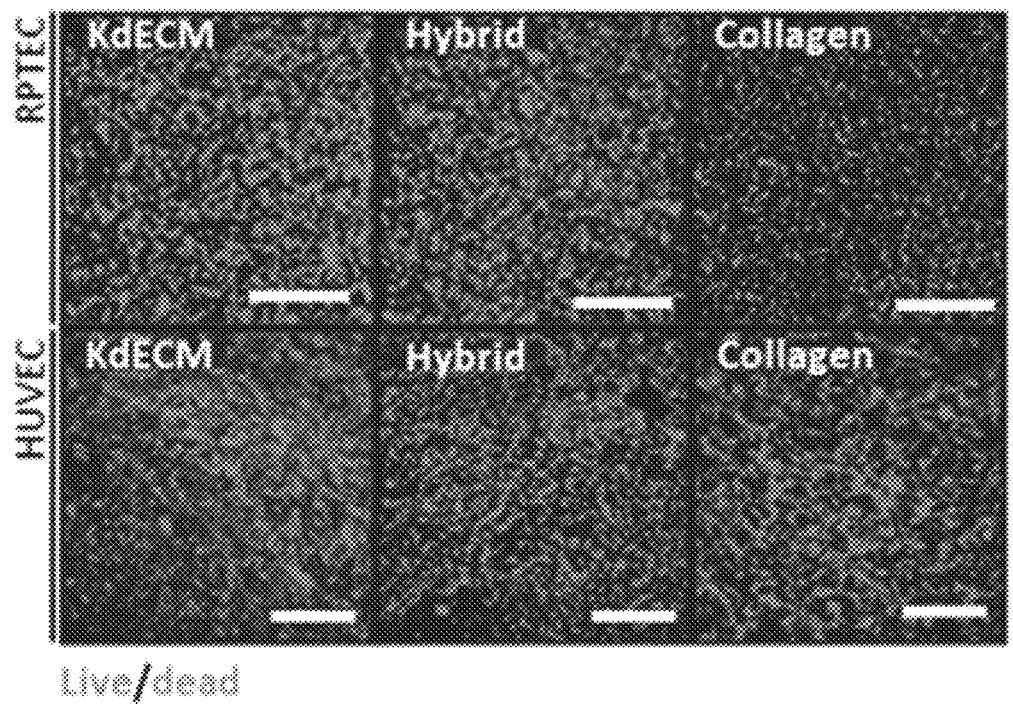

FIG. 4A and FIG. 4B are diagrams illustrating results of confirming a mixing ratio and cytotoxicity of hybrid bioink.

Meanwhile, alginate may be included in the decellularized substance to maintain the construct after printing the bioink. Since a difference may occur in the cell viability depending on a ratio of the alginate mixed with the decellularized substance, the alginate may be determined and mixed in a ratio that minimizes cytotoxicity while maintaining an appropriate strength. As an example, after mixing, a final concentration of the hybrid bioink may be 30 mg/ml for the decellularized substance and 10 mg/ml for the alginate. Meanwhile, referring to FIG. 4A, it can be confirmed that the kidney functional marker is expressed according to a ratio of the decellularized substance and the alginate in order to confirm the cell viability. In addition, referring to FIG. 4B, it was confirmed that the final hybrid bioink had no toxicity to the RPTECs and the HUVECs 1.

Hereinafter, a producing method of a perfusable-type dual proximal tubule cell construct according to a first embodiment according to the present disclosure will be described with reference to FIGS. 5 to 6.

Figure 5:
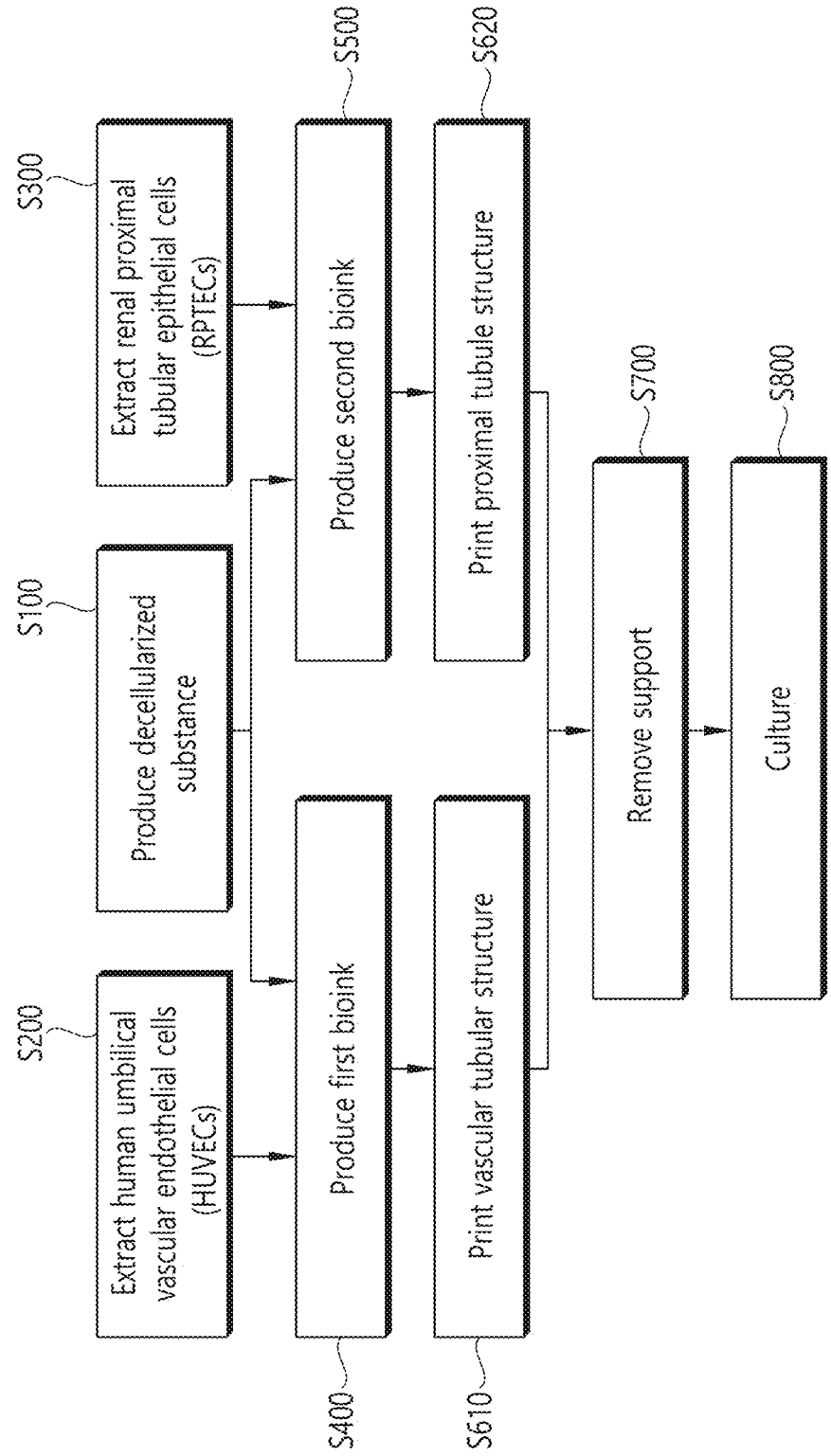
FIG. 5 is a flow chart of a producing method of a perfusable-type dual proximal tubule cell construct according to a first embodiment of the present disclosure.

FIG. 5 is a flow chart of a producing method of a perfusable-type dual proximal tubule cell construct according to a first embodiment of the present disclosure.

Referring to FIG. 5, the producing method of the perfusable-type dual proximal tubule cell construct according to the first embodiment of the present disclosure includes a decellularized substance producing step (S100), a HUVEC extracting step (S200), a RPTEC extracting step (S300), a first bioink producing step (S400), a second bioink producing step (S500), a coaxial tubular construct 3D printing step (S600), a support removing step (S700), and a culturing step (S800).

The decellularized substance producing step (S100) corresponds to a step of producing the hybrid bioink by the method described with reference to FIG. 2A and FIG. 2B.

The HUVEC extracting step (S200) corresponds to a step of extracting the HUVECs 1 to be cultured from a kidney tissue.

The RPTEC extracting step (S300) corresponds to a step of extracting the RPTECs 2 to be cultured.

Meanwhile, the extracted cells in the HUVEC extracting step (S200) and the RPTEC extracting step (S300) and the kidney tissue used in the decellularized substance producing step may be derived from different individuals, respectively, and may also be derived from different species, respectively.

The first bioink producing step (S400) corresponds to a step of producing a final substance for printing by encapsulating the HUVECs 1 in the aforementioned hybrid bioink.

The second bioink producing step (S500) corresponds to a step of producing a final substance for printing by encapsulating the RPTECs 2 in the aforementioned hybrid bioink.

The coaxial tubular construct 3D printing step (S600) corresponds to a step of printing a dual tubular construct using the first bioink 10 and the second bioink 20. The coaxial tubular construct 3D printing step (S600) may be performed using a nozzle 3 consisting of a triple coaxial nozzle 3. The triple coaxial nozzle 3 may be configured to include a circular opening formed in a center portion thereof and two annular openings formed in an outer side of the circular opening and having different diameters, and may be configured to print different materials in each opening.

As an example, in the coaxial tubular construct 3D printing step (S600), a support 300 may be printed using support ink 30 to maintain a shape in which the dual tubular construct to be described below is printed in the center portion thereof. The support 300 may be made of a material that is able to be easily removed without affecting the dual tubular construct to be printed below. As an example, the support 300 may be produced by printing 30% Pluronic F127 (CPF127) mixed with 100 mM $CaCl_2$. The first bioink 10 may be printed on the outer periphery of the support 300 so that a first tubular construct 100 that simulates a blood vessel may be printed. A second tubular construct 200 that simulates the proximal tubule may be printed on the outer periphery of the first tubular construct 100.

Meanwhile, the CPF127 in the support 300 serves to cross-link alginate while the first bioink 10 and the second bioink 20 are printed and helps to maintain the construct of the first bioink 10 and the second bioink 20 having a weak strength.

In the coaxial tubular construct 3D printing step (S600), the aforementioned support 300, the first tubular construct 100, and the second tubular construct 200 may be simultaneously printed using the triple coaxial nozzle 3.

The support removing step (S700) corresponds to a step of removing the unnecessary support 300 in the cell culturing process after printing. The support removing step (S700) corresponds to a step of dissolving and removing the CPF127, which has been used as the support 300, in a cell culture medium.

The culturing step (S800) is a step of culturing cells in the dual tubular construct to reproduce an artificial organ of a tissue unit.

Figure 6A:
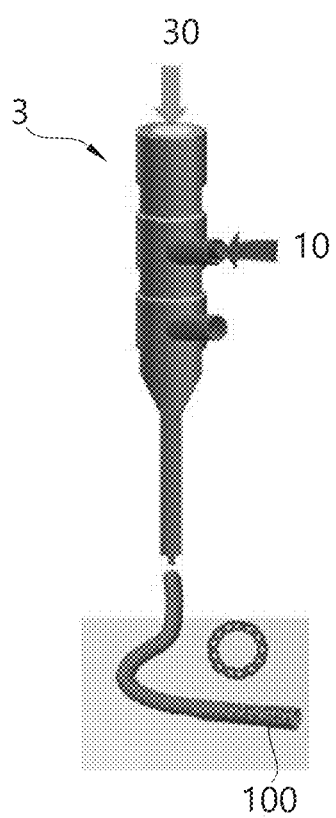
FIG. 6A, FIG. 6B and FIG. 6C are schematic diagrams illustrating a concept of 3D-printing a tubular construct using the first bioink and the second bioink.
Figure 6B:
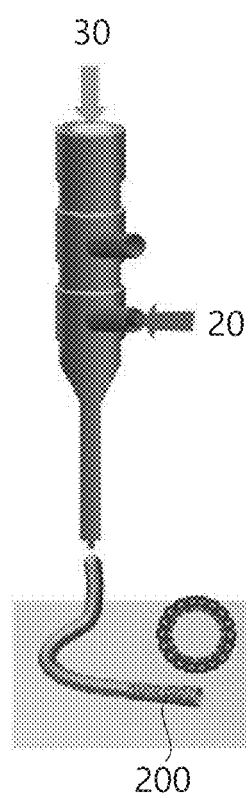
Figure 6C:
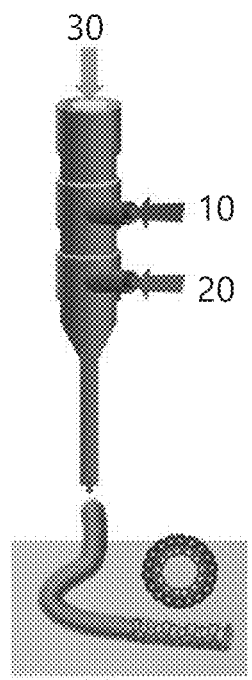

FIG. 6A, FIG. 6B and FIG. 6C are schematic diagrams illustrating a concept of 3D-printing the tubular construct using the first bioink 10 and the second bioink 20.

As illustrated in FIG. 6A, FIG. 6B and FIG. 6C, the support 300 and the first tubular construct 100 are simultaneously printed using the triple coaxial nozzle 3 (FIG. 6A), or the support 300 the second tubular construct 200 may be simultaneously printed using the triple coaxial nozzle 3 (FIG. 6B). In addition, the support 300, the first tubular construct 100, and the second tubular construct 200 may be simultaneously printed concentrically using the triple coaxial nozzle 3 (FIG. 6C).

Figure 7:
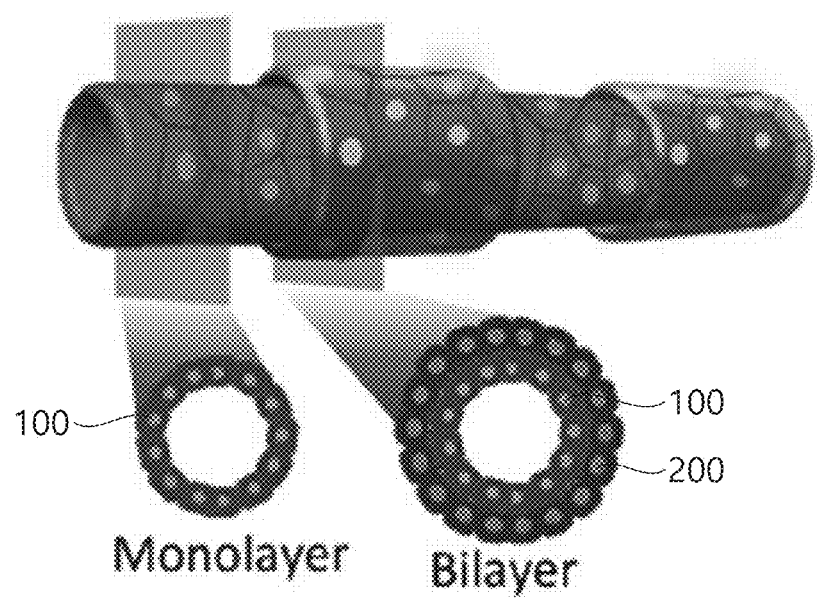
FIG. 7 is a diagram illustrating a concept of printing a dual proximal tubule cell construct according to a second embodiment of the present disclosure.

FIG. 7 is a diagram illustrating a concept of printing a dual proximal tubule cell construct according to a second embodiment of the present disclosure.

As illustrated in FIG. 7, in the present disclosure, the support 300 may be printed in a triple construct using the triple coaxial nozzle 3, and after printing, the support 300 may be removed to complete a dual tubular construct. In addition, the dual tubular construct and a single tubular construct may be selectively printed at multiple points along a longitudinal direction of the tubular construct, that is, a direction parallel to a concentric axis, by using the coaxial nozzle 3. That is, the printed tubular construct may include a dual tubular construct in at least a part thereof, or may also include the dual tubular construct at multiple points.

Figure 8A:
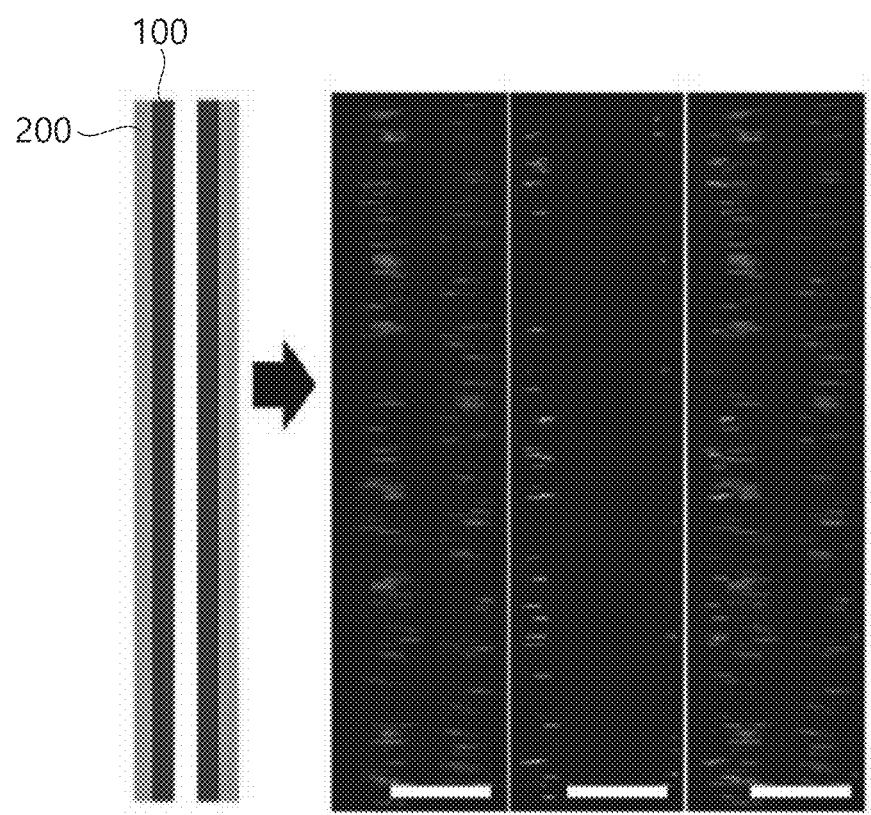
FIG. 8A and FIG. 8B are diagrams illustrating a fluorescence image of a cross section of the second embodiment.
Figure 8B:
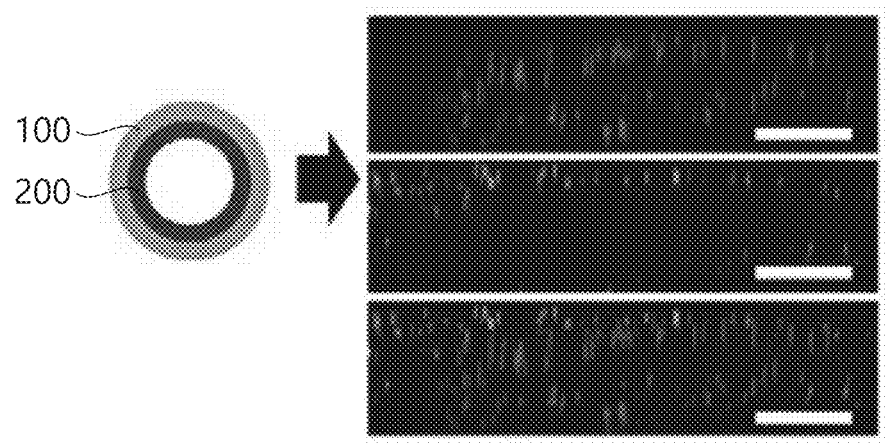

FIG. 8A and FIG. 8B are diagrams illustrating a fluorescence image of a cross section of the second embodiment. As illustrated, as a result of obtaining a fluorescence image for the 3D-printed dual tubular construct according to the first embodiment, longitudinal cross section (8A) and radial cross section (8B) can be confirmed that the first (inner) tubular construct 100 (bright white) and the second (outer) tubular construct 200 (dark white) each has a cylindrical construct, that is, a tubular construct, and has maintained the construct.

Hereinafter, a producing method of a proximal tubule cell construct according to a third embodiment according to the present disclosure will be described in detail with reference to FIG. 9. The present embodiment may also include the same configurations as the above-described embodiment, and the description of these configurations will be omitted in order to avoid redundancy and only different configurations will be described.

Figure 9:
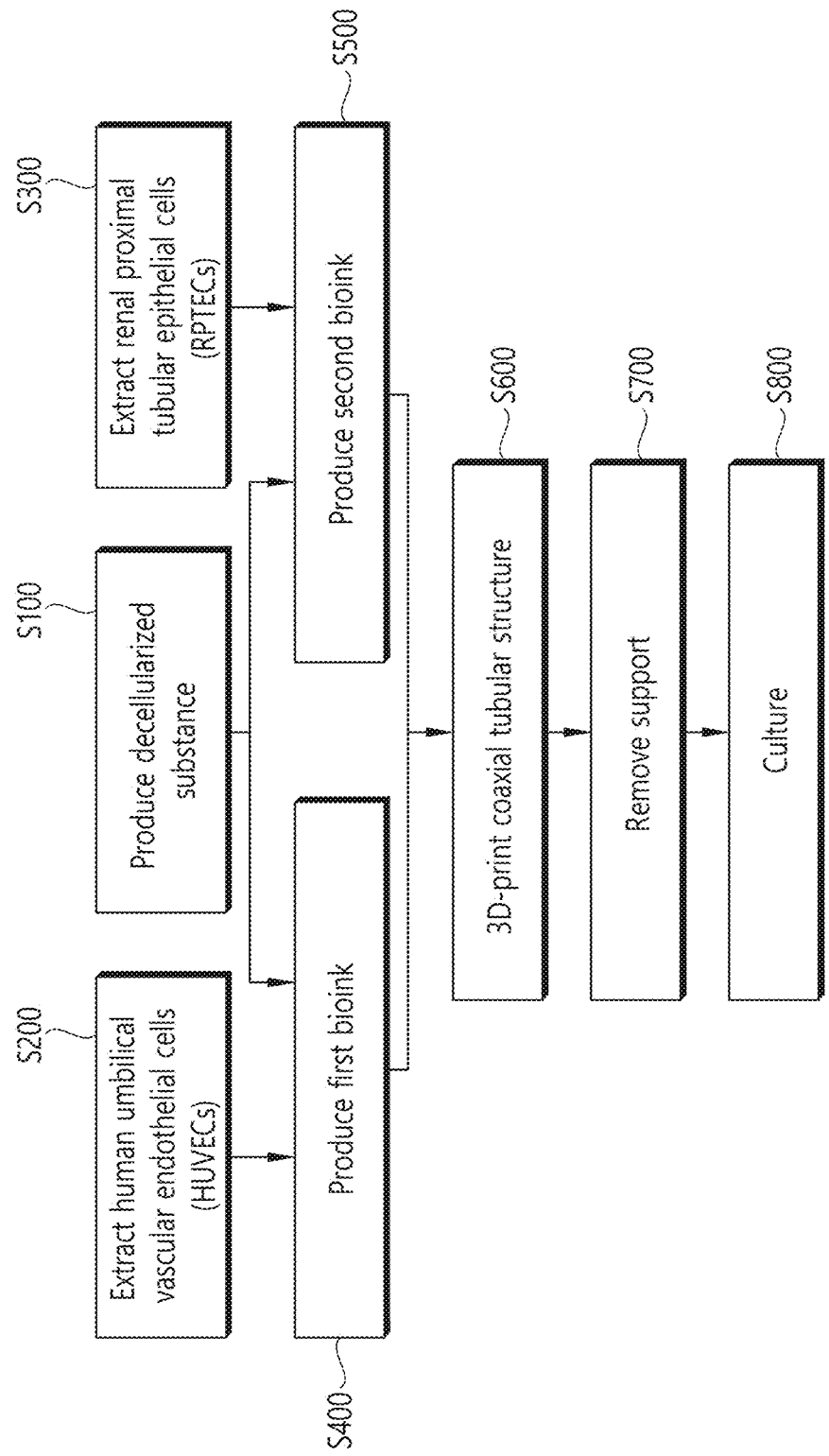
FIG. 9 is a flow chart of a producing method of a perfusable-type proximal tubule cell construct according to a third embodiment of the present disclosure.

FIG. 9 is a flow chart of a producing method of a perfusable-type proximal tubule cell construct according to a third embodiment of the present disclosure.

As illustrated in FIG. 9, the producing method of the perfusable-type proximal tubule cell construct according to the third embodiment of the present disclosure may include printing a vascular tubule construct and a proximal tubule construct that are not concentric with each other, respectively.

A vascular tubule construct printing step (S610) is a step of preparing a first bioink 10 and then printing the vascular tubule construct using the first bioink 10.

A proximal tubule construct printing step (S620) is a step of preparing a second bioink 20 and then printing the proximal tubule construct using the second bioink 20.

Meanwhile, each support 300 is printed together in central portions of the vascular tubule construct and the proximal tubule construct to maintain the tubular construct. In addition, at least portions of the outer surfaces of the vascular tubule construct and the proximal tubule construct may be in contact with each other.

On the other hand, after printing, the support removing step (S700) and the culturing step (S800) may be performed similarly to those of the first embodiment.

Meanwhile, although not illustrated, in the third embodiment, a case 1000 for culturing may be printed before and after printing of the perfusable-type proximal tubule cell construct. That is, a separate 3D printer nozzle 3 for printing the case 1000 is provided, and a lower surface of the case 1000 is printed, the tubular construct is printed, and thereafter, the remaining portion of the case 1000 may be printed so as to accommodate the culture solution while surrounding at least a part of the tubular construct.

Figure 10:
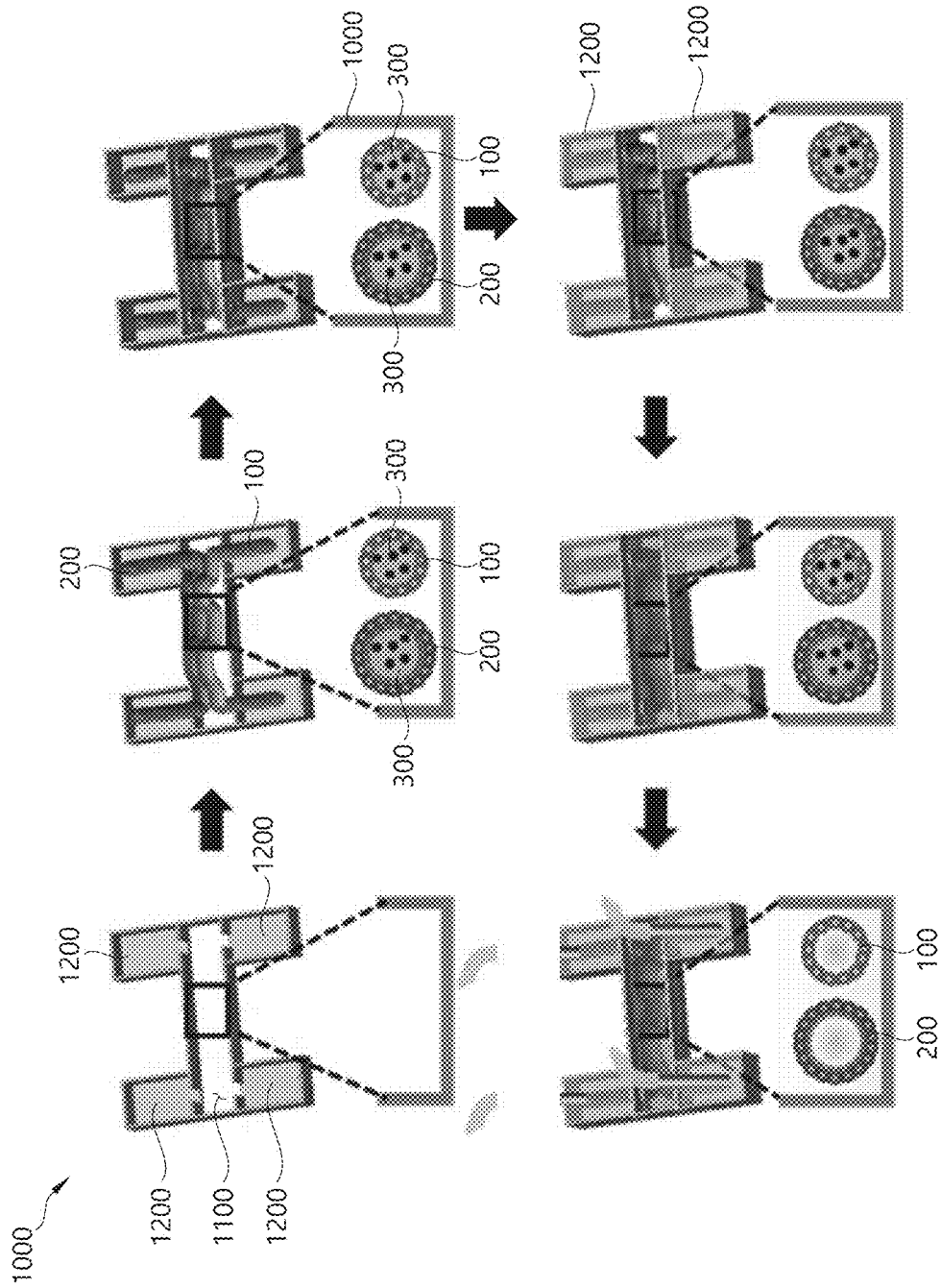
FIG. 10 is a schematic diagram of an renal proximal tubule-on-a-chip which is a fourth embodiment produced by the producing method of the perfusable-type proximal tubule cell construct according to the third embodiment of the present disclosure.

FIG. 10 is a schematic diagram of an renal proximal tubule-on-a-chip which is a fourth embodiment produced by the producing method of the perfusable-type proximal tubule cell construct according to the third embodiment of the present disclosure. Referring to FIG. 10, the renal proximal tubule-on-a-chip may be configured to include a case 1000 and a perfusable-type proximal tubule chip.

The case 1000 may be configured to include an artificial proximal tubule part 1100 configured to dispose the perfusable-type proximal tubule chip, and a fixing part 1200 capable of fixing the inner side of each tube of the perfusable-type proximal tubule to fluidly communicate with the outer side. Referring back to FIG. 10, the artificial proximal tubule part 1100 extending to a predetermined length in a horizontal direction is provided in the center portion of the drawing, and in the drawing, four fixing parts 1200 may be provided in both vertical directions, respectively. Here, both ends of the vascular tubule construct may be connected to the two fixing parts 1200 located on the lower side in the drawing, respectively. In addition, both ends of the proximal tubule construct may be connected to the two fixing parts 1200 on the upper side in the drawing, respectively.

Meanwhile, the lower surface of the case 1000 may be 3D-printed with a synthetic polymer, and as an example, may be composed of a PCL material. Thereafter, after printing the tubular construct, a sidewall and an upper surface of the case 1000 may be printed with the same material as the lower surface thereof.

After printing the case 1000, the ends of the tubular construct exposed to the fixing part 1200 are crosslinked by filling a biomaterial such as PDMS or agarose, respectively. Thereafter, the proximal tubule construct may be cultured by perfusing the cell culture solution from the outside to each tubular construct.

Figure 11A:
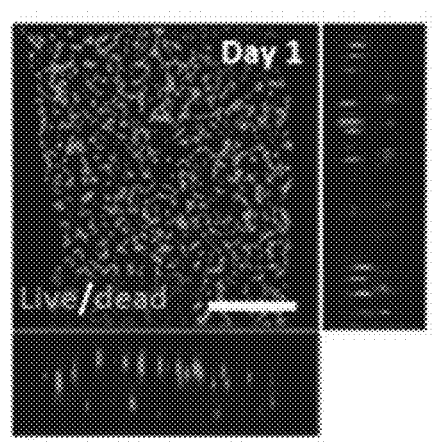
FIG. 11A and FIG. 11B are diagrams illustrating a concept of printing a first tubular construct using the first bioink and cell viability in the fourth embodiment.
Figure 11B:
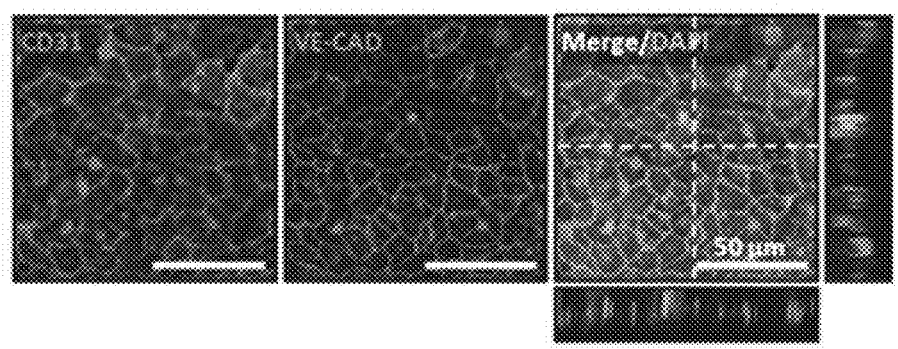
Figure 12:
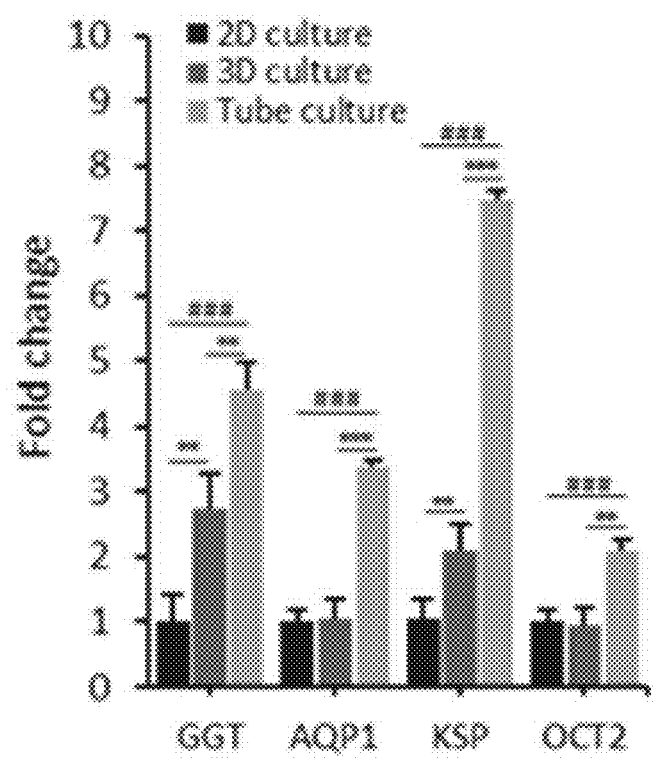
FIG. 12 is a diagram illustrating a difference in expression effect of a kidney functional marker between a case of producing the first tubular construct using the first bioink in the fourth embodiment and a case of printing the first tubular construct in simple 2D and simple 3D.

FIG. 11A and FIG. 11B are diagrams illustrating a concept of printing the first tubular construct 100 using the first bioink 10 and cell viability in the fourth embodiment and FIG. 12 is a diagram illustrating a difference in expression effect of a kidney functional marker between a case of producing the first tubular construct 100 using the first bioink 10 in the fourth embodiment and a case of printing the first tubular construct in simple 2D and simple 3D.

Referring to FIG. 11A, the cell viability may be confirmed when the first tubular construct 100 was 3D-printed using the first bioink 10, and referring to FIG. 11B, a functional marker of the HUVECs 1 on the 14th day after culturing may be confirmed, and it may be confirmed that the HUVECs 1 are proliferated smoothly.

Referring to FIG. 12, the expression levels of functional markers, for example, CD31 and VE-CAD according to a printing construct may be compared with each other in the same culture environment. When the first bioink 10 was printed in a 2D construct, a simple 3D construct, and a tubular construct, it may be confirmed that the expression level of the functional marker was the largest when the first bioink 10 was printed in the tubular construct.

Figure 13A:
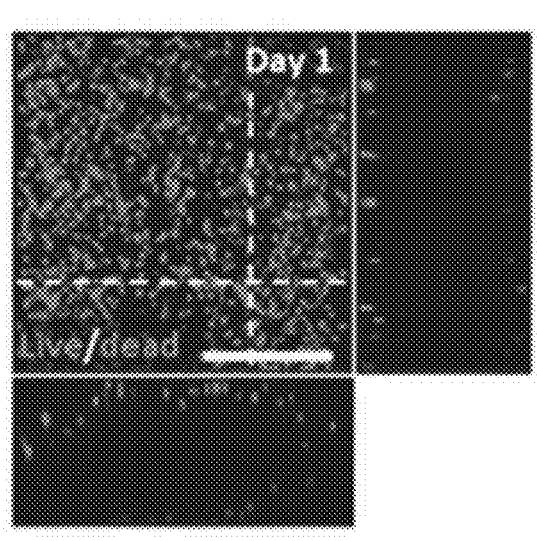
FIG. 13A and FIG. 13B are diagrams illustrating a concept of printing a second tubular construct using the second bioink and cell viability in the fourth embodiment.
Figure 13B:
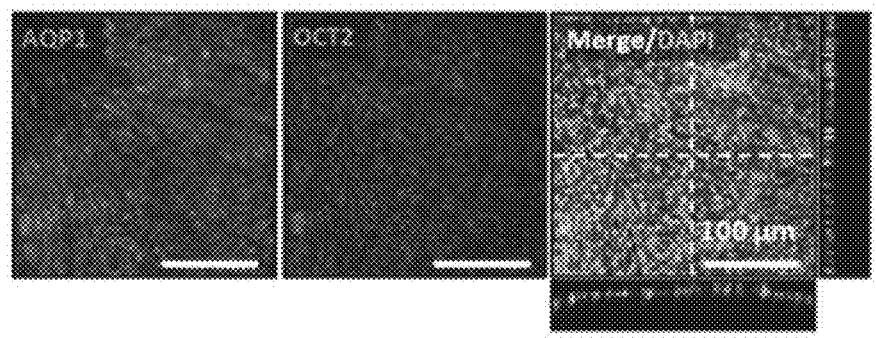
Figure 14:
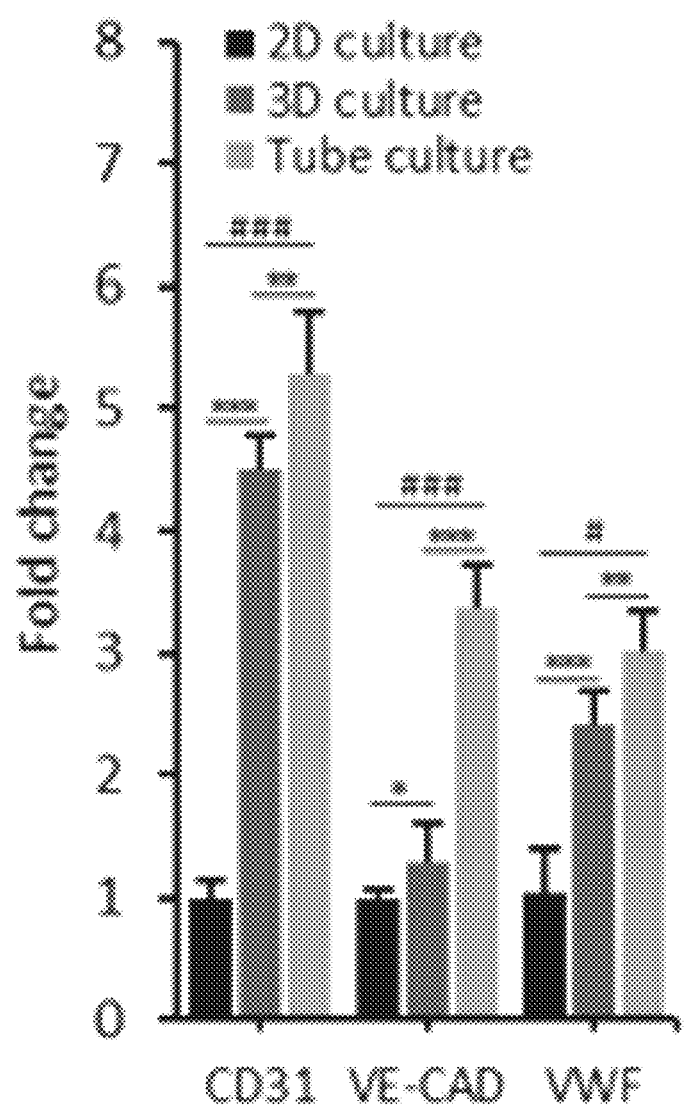
FIG. 14 is a diagram illustrating a difference in an expression effect of a kidney functional marker between a case of producing the second tubular construct using the second bioink in the fourth embodiment and a case of printing the second tubular construct in simple 2D and simple 3D.

FIG. 13A and FIG. 13B are diagrams illustrating a concept of printing the second tubular construct 200 using the second bioink 20 and cell viability in the fourth embodiment and FIG. 14 is a diagram illustrating a difference in expression effect of a kidney functional marker between a case of producing the second tubular construct 200 using the second bioink 20 in the fourth embodiment and a case of printing the second tubular construct in simple 2D and simple 3D.

Referring to FIG. 13A, the cell viability may be confirmed when the second tubular construct 200 was 3D-printed using the second bioink 20, and referring to FIG. 13B, a functional marker of the RPTECs 2 on the 14th day after culturing may be confirmed, and it may be confirmed that the RPTECs 2 are proliferated smoothly.

Referring to FIG. 14, the expression levels of functional markers, for example, GGT, AQP1, KSP, and OCT2 according to a printing construct may be compared with each other in the same culture environment. When the second bioink 20 was printed in a 2D construct, a simple 3D construct, and a tubular construct, it may be confirmed that the expression level of the functional marker was the largest when the second bioink 20 was printed in the tubular construct.

Figure 15:
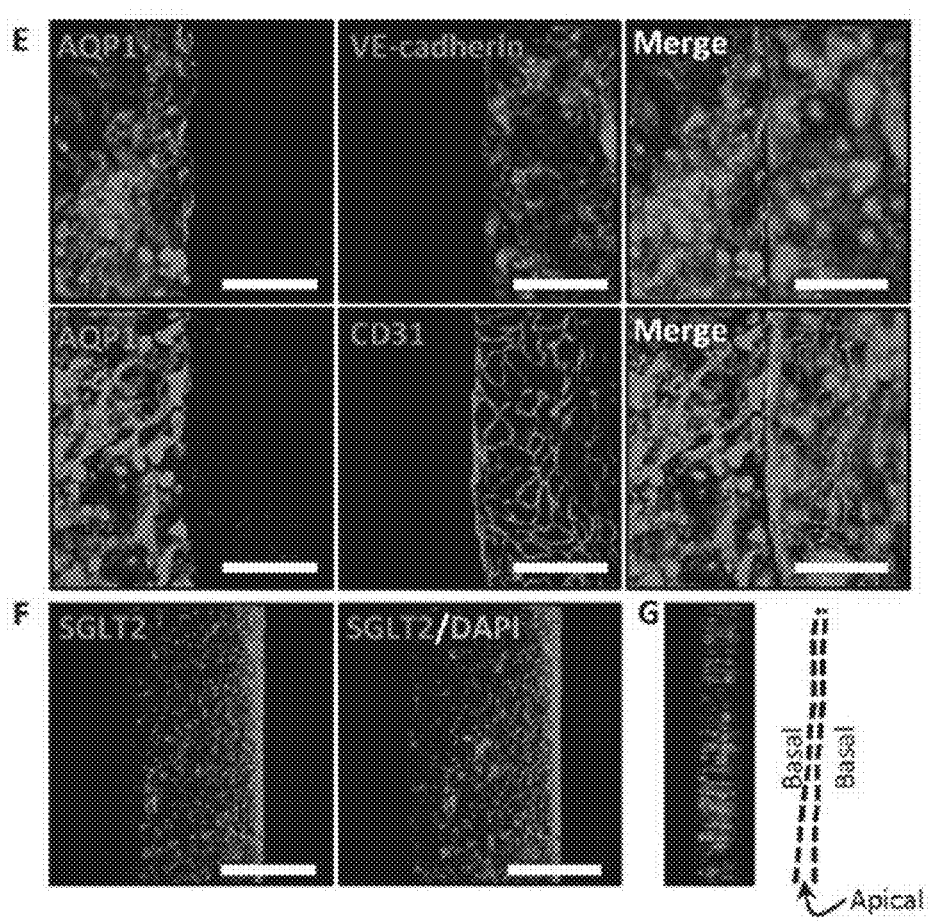
FIG. 15 is a diagram illustrating a construct confirmed through a marker of each tubular tissue after culturing for 28 days in the fourth embodiment.

FIG. 15 is a diagram illustrating a construct confirmed through a marker of each tubular tissue after culturing for 28 days in the fourth embodiment.

Referring to FIG. 15, an image of a portion in which the first tubular construct 100 and the second tubular construct 200 are in close contact with each other may be confirmed. It can be confirmed that in the first tubular construct 100, functional markers CD31 and VE-cadherin of the HUVECs 1 are expressed, and in the second tubular construct, a functional marker AQP1 of the RPTECs 2 is expressed, and it can be confirmed that proliferation has occurred while a boundary between printed tubular constructs is formed. In addition, in the second tubular construct 200, the atypical expression of sodium-glucose cotransporter-2 (SGLT2) has the polarity of the RPTECs 2.

Figure 16A:
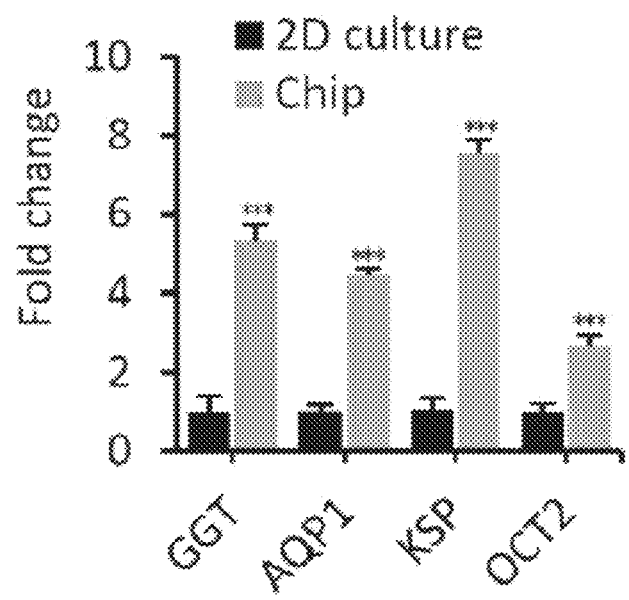
FIG. 16A and FIG. 16B are diagrams illustrating a difference in expression effect of a kidney functional marker between a case of culturing the fourth embodiment for 28 days and a case of simple 2D printing.
Figure 16B:
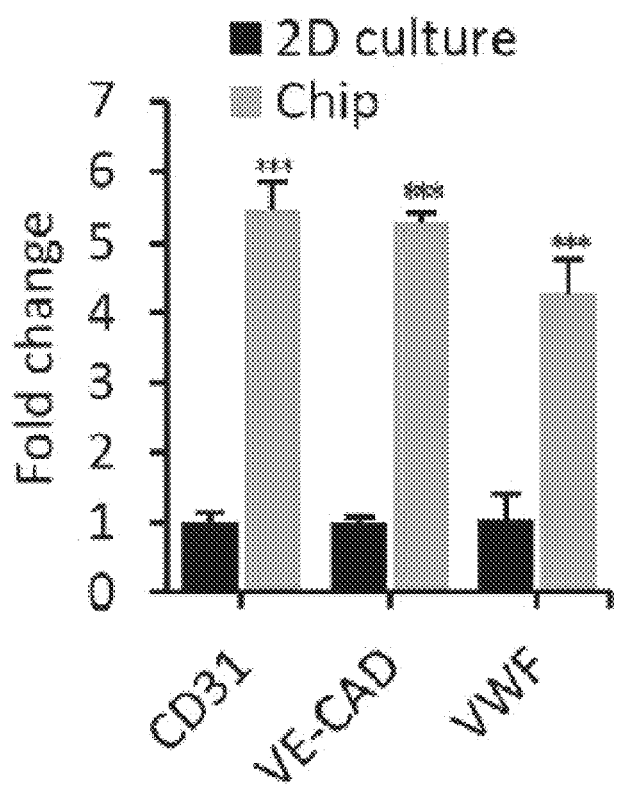

FIG. 16A and FIG. 16B are diagrams illustrating a difference in expression effect of a kidney functional marker between a case of culturing the fourth embodiment for 28 days and a case of simple 2D printing.

Referring to FIG. 16A and 16B, it can be confirmed that a result of functional marker expression in an occlusal construct of the first tubular construct 100 and the second tubular construct 200 increases significantly compared to the conventional 2D culture and conventional 3D culture construct, thereby providing an advantageous environment.

As described above, in the perfusable-type proximal tubule cell construct and the producing method thereof capable of applying the in vitro artificial organ model according to the present disclosure, it is possible to mature the tubular cell constructs on the perfusional-based renal proximal tubule-on-a-chip. Therefore, it is possible to use the renal proximal tubule-on-a-chip as a bioreactor capable of observing a biological drug reaction similar to the real drug by perfusing various drugs to the renal proximal tubule-on-a-chip.

According to the present disclosure, the perfusable-type proximal tubule cell construct and the producing method thereof capable of applying the in vitro artificial organ model can be extended and applied to bio-artificial kidneys for regenerative medicine as well as in vitro kidney models.

What is claimed is:

1. A perfusable-type bio-dual proximal tubule cell construct comprising:
   a first bioink comprising a decellularized substance derived from a mammalian kidney tissue and human umbilical vascular endothelial cells (HUVECs); and
   a second bioink comprising the decellularized substance and renal proximal tubular epithelial cells (RPTECs),
   wherein the first bioink and the second bioink are coaxial and printed in tubular constructs having different inner diameters.

2. The perfusable-type bio-dual proximal tubule cell construct of claim 1, wherein the first bioink is printed to configure a first tubular construct, the second bioink is printed to configure a second tubular construct, and at least a part of an outer surface of the first tubular construct is configured to be in contact with an inner surface of the second tubular construct.

3. The perfusable-type bio-dual proximal tubule cell construct of claim 2, wherein the first bioink and the second bioink are configured to include alginate so as to reduce a shape change after printing.

4. The perfusable-type bio-dual proximal tubule cell construct of claim 3, wherein the first bioink and the second bioink are configured to comprise the decellularized substance in a concentration of 20 mg/ml to 40 mg/ml and the alginate in a concentration of 5 mg/ml to 15 mg/ml.

5. The perfusable-type bio-dual proximal tubule cell construct of claim 4, wherein the decellularized substance is produced in the form of a hydrogel by lyophilizing the kidney tissue, treating the lyophilized kidney tissue with 0.3 M to 0.7 M of an acetic acid solution, and neutralizing the treated kidney tissue with 5 M to 15 M NaOH.

6. The perfusable-type bio-dual proximal tubule cell construct of claim 3, wherein the first tubular construct and the second tubular construct are simultaneously printed by a 3D printer provided with a coaxial double nozzle.

7. The perfusable-type bio-dual proximal tubule cell construct of claim 4, further comprising:

a support configured to support the first tubular construct from the inner side of the first tubular construct and configured to be removed when the tubule cell construct is cultured.

8. The perfusable-type bio-dual proximal tubule cell construct of claim 7, wherein the support is printed on the inner side of the first tubular construct while being coaxial with the first tubular construct and the second tubular construct.

9. The perfusable-type bio-dual proximal tubule cell construct of claim 7, wherein the support is produced by printing support ink comprising (polyethylene oxide-b-polypropylene oxide-b-polyethylene oxide.

10. An renal proximal tubule-on-a-chip comprising:

a vascular tubule construct which is printed with a first bioink comprising a decellularized substance derived from a mammalian kidney tissue and human umbilical vascular endothelial cells (HUVECs) and configured in a tubular shape; and a proximal tubule construct which is printed with a second bioink comprising the decellularized substance and renal proximal tubular epithelial cells (RPTECs) and configured in a tubular shape, wherein the vascular tubule construct and the proximal tubule construct are at least partially printed in parallel with each other and configured so that the outer surfaces thereof are in contact with each other.

11. The renal proximal tubule-on-a-chip of claim 10, further comprising:

a case provided with a space in which the vascular tubule construct and the proximal tubule construct are printed.

12. The renal proximal tubule-on-a-chip of claim 11, wherein the case comprises:

an artificial proximal tubule part configured to dispose a part of the vascular tubule construct and a part of the proximal tubule construct which are in contact with each other; and multiple fixing parts configured to fix both ends of the vascular tubule construct and both ends of the proximal tubule construct, respectively.

13. The renal proximal tubule-on-a-chip of claim 10, wherein the vascular tubule construct is printed by including a support that is coaxial with the first bioink and printed together on the inner side of the tubular part when the first bioink is printed, and is formed by removing the support after printing.

14. The renal proximal tubule-on-a-chip of claim 10, wherein the proximal tubule construct is printed by including a support that is coaxial with the second bioink and printed together on the inner side of the tubular part when the second bioink is printed, and is formed by removing the support after printing.

15. A producing method of a proximal tubule cell construct comprising the steps of:

producing a decellularized substance derived from a mammalian kidney tissue;

extracting and preparing human umbilical vascular endothelial cells (HUVECs) and renal proximal tubular epithelial cells (RPTECs) from a living kidney tissue;

producing a first bioink comprising the decellularized material and the HUVECs;

producing a second bioink comprising the decellularized material and the RPTECs;

printing a vascular tubule construct using the first bioink; and printing a proximal tubule construct using the second bioink, wherein the printing of the vascular tubule construct and the printing of the proximal tubule construct are performed while the vascular tubule construct and the proximal tubule construct are at least partially in contact with each other.

16. The producing method of the proximal tubule cell construct of claim 15, wherein the printing of the vascular tubule construct and the printing of the proximal tubule construct are performed using a coaxial triple nozzle, and a support on a central side, the vascular tubule construct on the outer side of the support, and the proximal tubule construct on the outer side of the vascular tubule construct are simultaneously printed coaxially.

17. The producing method of the proximal tubule cell construct of claim 15, wherein the printing of the vascular tubule construct is performed using a coaxial double nozzle, and is performed by printing a support configured to support the vascular tubule construct from the inner side of the vascular tubule construct simultaneously with the vascular tubule construct.

18. The producing method of the proximal tubule cell construct of claim 17, wherein the printing of the proximal tubule construct is performed using a coaxial double nozzle, and is performed by printing a support configured to support the proximal tubule construct from the inner side of the proximal tubule construct simultaneously with the proximal tubule construct.

19. The producing method of the proximal tubule cell construct of claim 18, wherein the printing of the vascular tubule construct and the printing of the proximal tubule construct are performed while the vascular tubule construct and the proximal tubule construct are at least partially parallel to each other and the outer surfaces thereof are in contact with each other.

20. The producing method of the proximal tubule cell construct of claim 16, further comprising:
  removing the support.

* * * * *